United States Patent [19]

Serur et al.

[11] 4,096,879
[45] Jun. 27, 1978

[54] ADJUSTABLE FLUID FLOW REGULATOR

[75] Inventors: Juan Ricardo Serur, Brookline; Herbert Heinz Loeffler, Arlington, both of Mass.

[73] Assignee: International Biomedical Laboratories, Inc., Boston, Mass.

[21] Appl. No.: 726,591

[22] Filed: Sep. 27, 1976

Related U.S. Application Data

[63] Continuation-in-part of Ser. No. 715,907, Aug. 19, 1976, abandoned.

[51] Int. Cl.² ............................................. F16k 21/18
[52] U.S. Cl. ........................... 137/391; 128/214 C; 137/423; 137/433; 137/453; 138/45; 222/68; 251/121; 251/206
[58] Field of Search ............ 128/214 C, 214 R, 214.2, 128/227; 137/391, 423, 426, 430, 433, 453; 222/56, 68; 251/118, 121, 205, 206, 207, 208; 138/45 A

[56] References Cited

U.S. PATENT DOCUMENTS

| 1,621,876 | 3/1927 | Doerr | 138/45 A |
| 1,831,318 | 11/1931 | O'Neil et al. | 137/423 |
| 1,926,413 | 9/1933 | Tibbs | 138/45 A |
| 2,090,273 | 8/1937 | Wagner | 137/391 |
| 2,602,464 | 7/1952 | Greening | 137/391 |
| 3,233,457 | 2/1966 | Martinez | 251/206 |
| 3,756,233 | 9/1973 | Goldowsky | 128/214 C |
| 3,877,428 | 4/1975 | Seagle | 251/208 |
| 3,929,157 | 12/1975 | Serur | 137/453 |
| 3,931,818 | 1/1976 | Goldowsky | 128/214 C |
| 3,989,043 | 11/1976 | Dimeff | 128/214 C |

OTHER PUBLICATIONS

Lancet - Apr. 6, 1963, pp. 754-755.

Primary Examiner—Alan Cohan
Assistant Examiner—G. L. Walton

[57] ABSTRACT

A rate of flow regulator comprising upper and lower fluid chambers, the upper chamber having a double acting float valve to maintain a predetermined level of fluid therein, vent means venting each chamber to atmosphere, and metering means for regulating fluid flow to the lower chamber, the height of said upper chamber being adjustable relative to said metering means to change the fluid flow rate.

21 Claims, 7 Drawing Figures

ADJUSTABLE FLUID FLOW REGULATOR

This is a continuation-in-part of application Ser. No. 715,907, filed Aug. 19, 1976, now abandoned.

This invention relates to fluid flow regulators for gravity fed systems, particularly to regulators suitable for delivery of fluids in medical applications. The invention is an improvement of the regulator system disclosed in U.S. Pat. No. 3,929,157.

It is a principal object of this invention to provide a fluid flow regulator having an extended range of accurate flow rate adjustability. Another object is to minimize the amount of fluid required for operation of the regulator. It is a further object to provide a system adapted for use with fluid sources either isolating the fluid from atmospheric pressure, as in a fixed wall container, e.g., a bottle, or subjecting the fluid to atmospheric pressure, e.g., flexible wall plastic bags of the sort commonly used in medical contexts. Yet further objects of this invention are to provide a regulator of inexpensive design, which is simple to use and which incorporates desirable safety features for medical use.

In general, the invention features a regulator comprising upper and lower fluid chambers, each having a fluid flow inlet and outlet, the upper chamber outlet in fluid flow communication with the lower chamber fluid flow inlet, and each chamber having a vent to atmospheric pressure. The upper chamber includes means for maintaining a predetermined level of fluid therein. Metering means for metering fluid flow are located in the fluid flow path between the upper and lower chambers. The vertical distance between the metering means and the predetermined level in the upper chamber is adjustable for varying the fluid flow rate by adjusting the relative heights of the metering means and the predetermined level.

In preferred embodiments, the metering means comprises a plurality of different sized elongated orifices and the metering means is adjustable to place a selected one orifice in the fluid flow path for further flow rate adjustment; a double acting float valve in the upper chamber, for selectively opening and closing the inlet and outlet, maintains the upper chamber predetermined level; a double acting float valve in the lower chamber, for opening and closing the lower chamber inlet and outlet, closes the outlet when fluid in the lower chamber falls below a predetermined level; ribs are provided closely adjacent the top of the upper chamber float valve; separate vents are provided in the upper and lower chambers and the float valves close the inlets as fluid level increases to a predetermined level below the vents; the metering means is positioned on the lower chamber, and the chambers are separate, being connected by a flexible tube; the metering means comprises a plurality of elongated orifices defined by grooves or differing cross-sectional area on the exterior of a stem and covered by the flexible tube; the chambers are connected to a support and are relatively moveable therealong, the lower chamber fixed and the upper chamber moveable; the support is tubular and the chambers are mounted therewithin; and sets of indicia are provided on the tubular support corresponding to the flow rates with different metering orifices and with different spacings of the upper chamber predetermined level and said metering means.

Other objects, features and advantages of this invention will be apparent to those skilled in the art from the following detailed description of a preferred embodiment thereof, taken together with the accompanying drawings, in which.

Figure 1:
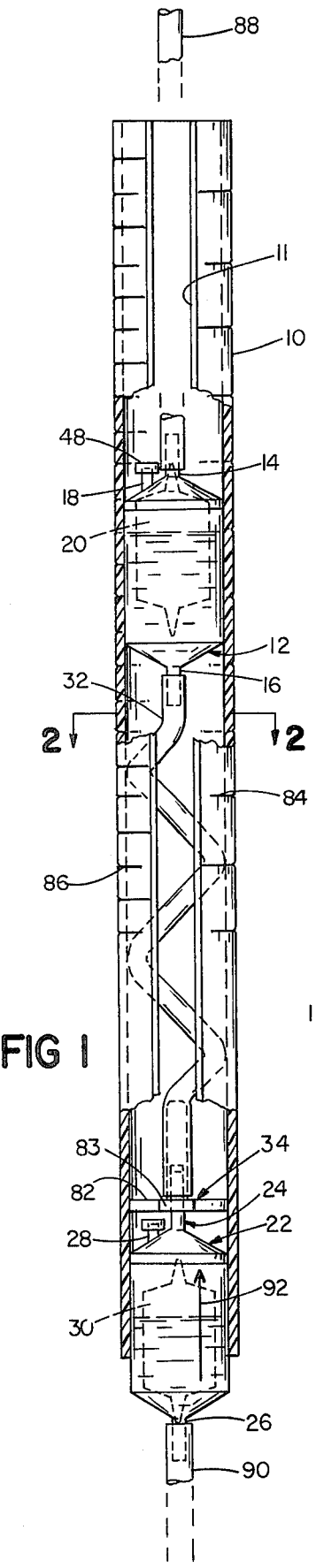
FIG. 1 is a side elevation, partially broken away, of a regulator embodying the invention.
Figure 2:
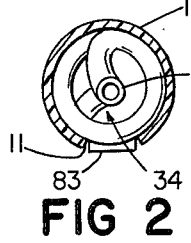
FIG. 2 is a sectional view taken along the line 2—2 of FIG. 1.

Referring now to the drawings and more particularly to FIG. 1 thereof, the regulator comprises a support 10 in the form of a vertically split tube having a vertical slot 11, as best shown in FIG. 2. Within support 10 are upper and lower chambers 12,22, each having a fluid inlet 14,24 and a fluid outlet 16,26, and each having a vent 18,28 to atmosphere. Within upper chamber 12 and also, in the preferred embodiment, within lower chamber 22 are double acting float valves 20,30 adapted selectively to open and close the chamber inlets 14,24 and outlets 16,26. Flexible tube 32 connects upper chamber outlet 16 to lower chamber inlet 24. Metering means 34 are mounted on lower chamber 22 for regulating flow from upper chamber 12. In the illustrated embodiment, upper chamber 12 is moveable along chamber support 10 to vary the fluid head therefrom to metering means 34 and hence the flow rate to lower chamber 22.

Figure 3:
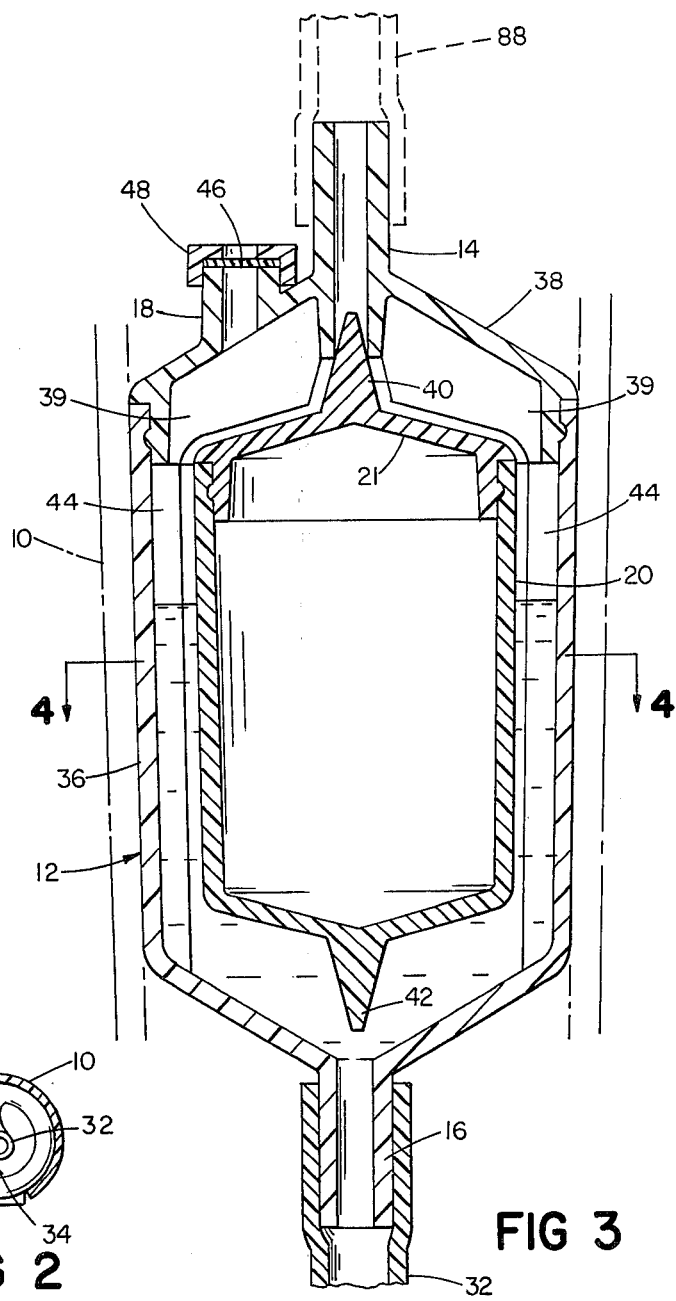
FIG. 3 is an enlarged sectional view of the upper fluid chamber, shown in FIG. 1.
Figure 4:
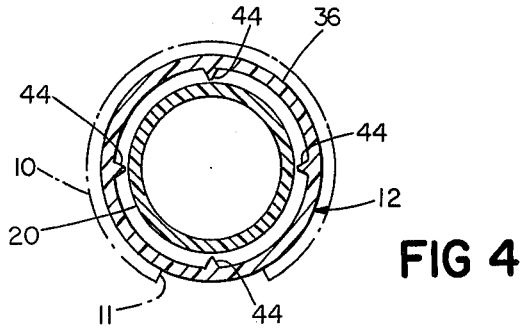
FIG. 4 is a reduced sectional view taken along the line 4—4 of FIG. 3.

In greater detail, upper chamber 12 is best shown in FIGS. 3 and 4. Chamber 12 comprises a tubular body 36 having outlet 16 at the bottom thereof. Chamber 12 also comprises a cover 38 having inlet 14 and vent 18 located therein. Double acting float valve 20 is positioned within chamber 12 and comprises conical valves 40,42 adapted selectively to open and close inlet 14 and outlet 16. Float valve 20 is centered within chamber 12 by ribs 44 integral with the walls of chamber body 36. Cover 38 also includes ribs or fins 39, aligned with ribs 44, which extend downwardly to a position spaced closely adjacent and parallel to the uppermost position of the outwardly sloped top 21 of float valve 20. Ribs 39 cause any fluid tending to accumulate on float valve 20 to flow away therefrom. Vent 18 is provided with a filter 46, secured by cap 48, to exclude contaminants from the chamber interior. Filter 46 is preferably a microporous hydrophobic membrane. Such membranes are available from Millipore Corporation of Bedford, Massachusetts.

Figure 5:
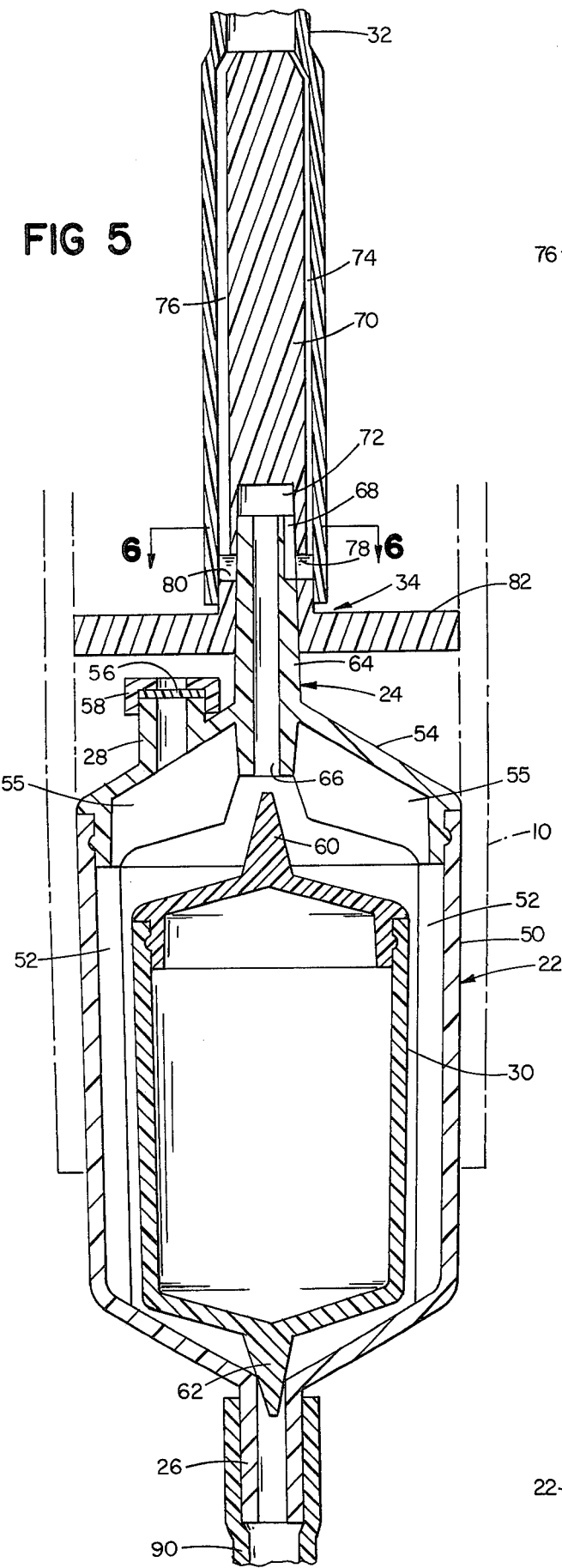
FIG. 5 is an enlarged sectional view of the lower fluid chamber, shown in FIG. 1, illustrating the metering means connected thereto.

As illustrated in FIG. 5, the lower fluid chamber 22 is of essentially the same construction as upper chamber 12, comprising a body 50 having integral ribs 52 centering double acting float valve 30 therewithin. Cover 54 contains inlet 24 and vent 28, which, like that of upper chamber 12, also is provided with a filter 56, preferably a microporous hydrophobic membrane, secured by a cap 58. Cover 54 may optionally also be provided with ribs 55 similar to ribs 39 of upper chamber cover 38. Float valve 30 is identical to valve 20 and has conical valves 60,62. Lower chamber 22 extends below support 10 to permit rotation thereof for adjustment of metering means 34, as hereinafter described.

Figure 6:
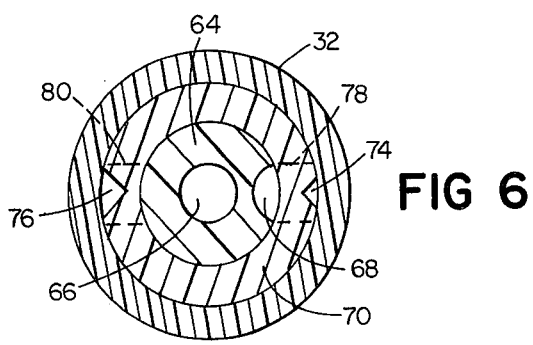
FIG. 6 is an enlarged sectional view taken along the line 6—6 of FIG. 5.
Figure 7:
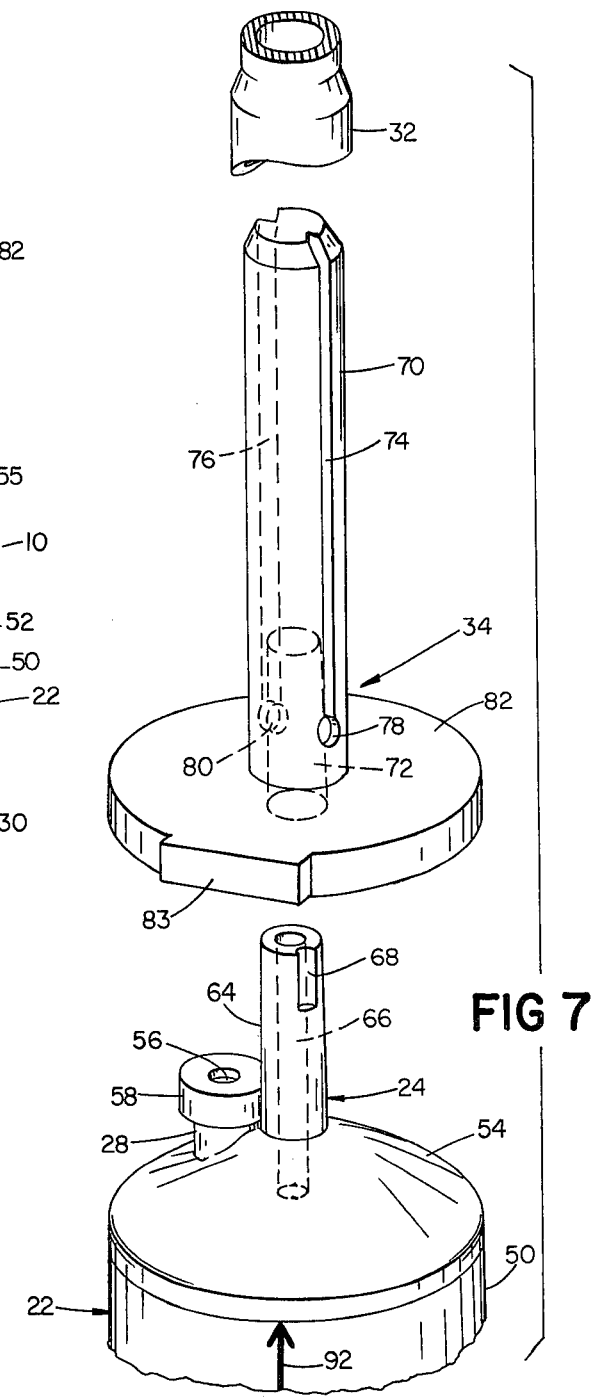
FIG. 7 is an exploded isometric view of the metering means shown in FIG. 5.

Metering means 34, on lower chamber 22 at inlet 24, is best illustrated in FIGS. 5, 6 and 7. Inlet 24 comprises a stem 64 extending above cover 54, tapered to receive metering means 34 thereon and, in addition to centrally positioned tubular inlet opening 66, is provided with a short vertical groove 68 on the exterior thereof at the end remote from cover 54. Metering means 34 comprises an elongated vertical stem 70 having a central tapered opening 72 therein adapted to rotatably fit on inlet stem 64 extending below groove 68 and spaced above the end of inlet stem 64. Metering orifices are provided by elongated vertical grooves 74,76 on the exterior of metering stem 70 on opposite sides thereof, extending from the end of stem 70 remote from lower chamber 22 to adjacent the base of groove 68 in inlet stem 64. Openings 78,80, at the bases of orifice grooves 74,76, extend through metering stem 70 from the bases of orifice grooves 74,76 to the base of inlet stem groove 68. Orifice grooves 74,76 have differing cross-sectional areas to permit different flow rates therethrough. Grooves 74,76 are closed by tube 32 extending over metering stem 70 to a position below openings 78,80. The elongated orifices, thus provided, advantageously result in a relatively linear change of fluid flow rate as chamber spacing is adjusted to alter fluid pressure. The covered groove arrangement provides an inexpensive and convenient way to make elongated orifices in the metering stem. Metering means 34 also comprises integral disc 82, below openings 78,80, having a diameter equal to that of lower chamber 22.

Chambers 12,22 and disc 82 have equal outer diameters which may be slightly greater than the inner diameter of the split tube chamber support 10 prior to assembly so that support 10 snugly engages the chambers 12,22 and disc 82 while permitting sliding movement within support 10 of upper chamber 12 and rotation of lower chamber 22 relative to metering means 34. Disc 82 includes a key 83 fitting the slot 11. Chambers 12,22, tube 10 and metering means 34 are of transparent plastic material, as is flexible tube 32, to permit visual observation of the regulator operation. Two sets of graduations 84,86 are preferably provided on tube 10 to indicate the spacing of chambers 12,22 in terms of the flow rates, depending on which metering orifice 74,76 is in use. Indicia 92 on lower chamber body 50 are provided to indicate the set of graduations which should be used.

In operation, the regulator is assembled with lower chamber 22 in a fixed position at the bottom of split tube chamber support 10. Upper chamber inlet 14 is connected by a tube 88 to a fluid source (not shown), chambers 12,22 are connected by tube 32, and lower chamber 22 is connected by a tube 90, e.g., to a patient (not shown). A fluid flow rate may then be selected first by rotating lower chamber 22 relative to metering means 34 to place a selected metering orifice 74,76 and its associated opening 78,80 in alignment with inlet stem groove 68; metering means 34 is held stationary by key 83 in slot 11 as chamber 22 is rotated. After the proper orifice is selected, further adjustment of flow rate is accomplished by spacing upper chamber 12 a selected distance from metering means 34, indicated by indicia 92 pointing to the appropriate set of graduations 84,86 corresponding to the orifice previously selected. Changes of flow rate in use may be made by adjusting the height of upper chamber 12, or, if necessary, by changing the orifice.

Fluid flows from the source into upper chamber 12 where float valve 20 operates to open and close inlet 14 and outlet 16, selectively to maintain a predetermined level of fluid therein, ribs 39 preventing fluid accumulation on valve 20. Fluid passes then through tube 32 and metering means 34 to lower chamber 22. The fluid flow path through metering means 34 extends along orifice groove 74, defined with tube 32, through opening 78, upwardly along groove 68 on inlet stem 64 to the space between the end of stem 64 and opening 72 and thence into inlet opening 66. Float valve 30, in lower chamber 22, serves as a check valve closing outlet 26 when fluid in lower chamber 22 falls to predetermined level, thereby preventing the passage of air through outlet 26. Float valves 20,30 also serve to close inlets 14,24 when fluid in chambers 12,22 increases to a predetermined level, below vents 18,28, thereby preventing fluid overflow through the vents 18,28.

Advantageously, the maintenance of a predetermined fluid level in upper chamber 12 and the venting of both chambers 12,22 to atmospheric pressure renders the flow rate dependent upon the spacing between the predetermined fluid level in the upper chamber and the metering orifice and upon the cross-sectional size of the metering orifice. The adjustment of the spacing provides an extended flow rate adjustment range which is further extended by the adjustable metering means for changing the orifice size. The elongated orifices result in relatively linear flow rate changes as spacing is adjusted. The microporous filters exclude bacteria from the regulator. The float valve in upper chamber, maintaining a predetermined fluid level therein, permits use of the regulator with either rigid or flexible wall fluid containers. Advantageously, also the float valves 20,30 occupy a major portion of the volumes of chambers 12,22 thus minimizing the amount of fluid contained in the regulator system, a particular advantage when small quantities of fluid are available or when the fluid is expensive. The regulator construction is simple and inexpensive to construct. Its use is simple, as well.

Other embodiments of this invention will occur to those skilled in the art which are within the scope of the following claims.

What is claimed is:

1. In a rate of flow regulator for use in a gravity assisted fluid delivery system, the regulator comprising: an upper fluid chamber having a fluid inlet and a fluid outlet and further having means for maintaining a predetermined level of fluid in said upper chamber; a separate lower fluid chamber having a fluid inlet and a fluid outlet; a flexible tube connecting said fluid inlet in fluid flow communication with said upper chamber fluid outlet; and vent means for communicating atmospheric pressure to each said chamber; the improvement in which structure defining a restricted metering orifice of predetermined cross-sectional area at said lower chamber fluid inlet in the fluid flow path from said upper chamber to said lower chamber for metering fluid flow to said lower chamber, said tube connected to said metering orifice structure; the vertical distance between said lower chamber and said upper chamber is adjustable to vary the distance between said metering orifice and said predetermined level in said upper chamber whereby fluid flow rate between said chambers may be adjusted by adjusting said vertical distance.

2. The improvement claimed in claim 1 in which said metering orifice is incrementally adjustable to change the cross-sectional size of said metering orifice and thereby change said flow rate.

3. The improvement claimed in claim 2 in which said metering orifice structure defines a plurality of metering orifices of differing cross-sectional areas and is adjustable to place a selected one of said orifices in said fluid flow path.

4. The improvement claimed in claim 1 in which said means for maintaining said predetermined level in said upper chamber comprises valve means in said upper chamber for opening and closing selectively said upper chamber inlet and outlet.

5. The improvement claimed in claim 1 in which said vent means includes a vent in said lower chamber and said lower chamber includes means for closing said inlet thereto when fluid in said lower chamber increases to a predetermined level below said vent in said lower chamber.

6. The improvement claimed in claim 5 in which said lower chamber comprises means at said outlet thereof closing said outlet thereof when fluid in said lower chamber is less than a predetermined amount.

7. The improvement claimed in claim 6 in which said means for closing said lower chamber inlet and said means for closing said lower chamber outlet comprise single means for selectively opening and closing said lower chamber inlet and outlet.

8. The improvement claimed in claim 7 in which said means for maintaining said predetermined level of fluid in said upper chamber and said single means for opening and closing said lower chamber inlet and outlet comprise double-acting float valves, one in each said chamber, for opening and closing the respective inlets and outlets of said upper and lower chambers.

9. The improvement claimed in claim 8 in which the top of said float valve in said upper chamber slopes outwardly and ribs connected to said chamber extend downwardly to a position spaced closely adjacent and above the top of the float valve and parallel to said top of said float valve in its uppermost position in said upper chamber.

10. The improvement claimed in claim 1 further including a chamber support, said chambers connected thereto and relatively adjustable therealong.

11. The improvement claimed in claim 10 in which said support has indicia of flow rates therealong corresponding to different spacings of said predetermined level and said metering orifice structure.

12. The improvement claimed in claim 10 in which said support comprises a tubular structure and said chambers are mounted within said structure.

13. The improvement claimed in claim 10 in which said lower chamber is mounted in a fixed position on said support and said upper chamber is movable therealong.

14. The improvement claimed in claim 13 in which said metering orifice is incrementally adjustable to change the cross-sectional size of said metering orifice and thereby change said flow rate.

15. The improvement claimed in claim 14 in which said metering orifice structure defines a plurality of metering orifices of differing cross-sectional areas and is adjustable to place a selected one of said orifices in said fluid flow path.

16. The improvement claimed in claim 15 in which said support comprises a tubular structure and said chambers are mounted within said structure.

17. The improvement claimed in claim 16 in which said support has sets of indicia of flow rates therealong corresponding to different distances of said predetermined level and said metering orifice structure and corresponding to the metering orifices in said metering orifice structure.

18. The improvement claimed in claim 17 in which said upper and lower chamber each have separate vents to atmosphere, said lower chamber includes means for regulating the level of fluid therein, and said means for maintaining said predetermined level of fluid in said upper chamber and for regulating the level of fluid in said lower chamber comprise double-acting float valves, one in each said chamber, for opening and closing the respective inlets and outlets of said chambers and adapted to maintain fluid levels respectively below said vents.

19. The improvement claimed in claim 1 in which said metering orifice structure comprises a metering stem connected to said lower chamber at said inlet thereof, said stem having a groove on the exterior thereof and said flexible tube extending over said stem and said groove defining with said tube an elongated metering orifice, one end of said orifice in fluid flow communication with said lower chamber inlet and the other end in fluid flow communication through said tube with said upper chamber outlet.

20. The improvement claimed in claim 19 in which said stem has a plurality of grooves of different cross-sectional areas, each covered by said tube, defining a plurality of orifices, said stem adjustable relative to said lower chamber inlet for selectively positioning a single one of said orifices in fluid flow communication with said lower chamber inlet.

21. The improvement claimed in claim 20 in which said lower chamber inlet comprises an inlet stem having a central opening therethrough and a vertical groove on one side thereof, said metering stem is rotatably positioned on said inlet stem and an opening extends from each said groove in said metering stem, at said one end thereof, therethrough to said inlet stem, whereby on relative rotation of said stems a particular orifice may selectively be placed in communication with said inlet by alignment of its opening through said metering stem with said inlet stem groove.

* * * * *